United States Patent [19]

Cherian

[11] Patent Number: 6,045,808
[45] Date of Patent: *Apr. 4, 2000

[54] METHOD FOR REMOVING HIGH BOILING SOLVENTS FROM DRUG FORMULATIONS BY VACUUM DRYING

[75] Inventor: Mathew Cherian, Albuquerque, N. Mex.

[73] Assignee: Pharmacia & Upjohn Company, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/791,935

[22] Filed: Jan. 31, 1997

[51] Int. Cl.$^7$ .............................. A61K 9/00; C07H 1/06; B01D 3/00
[52] U.S. Cl. .............................. 424/400; 203/56; 203/57; 203/63; 203/73; 536/127
[58] Field of Search .................................. 536/18.5, 124, 536/127; 203/56, 57, 63, 73; 424/400

[56] References Cited

U.S. PATENT DOCUMENTS 3,532,677 10/1970 Baron et al. ........................... 260/79.3

FOREIGN PATENT DOCUMENTS

| 143368 | 8/1980 | Germany . |
|---|---|---|
| 50-059275 | 5/1975 | Japan . |
| 58-207901 | 12/1983 | Japan . |
| 04193302 | 7/1992 | Japan . |
| 07126398 | 5/1995 | Japan . |
| 146137 | 12/1988 | Poland . |
| 94/12198 | 6/1994 | WIPO . |

OTHER PUBLICATIONS

Laskar et al., "Degradation of Carmustine in Mixed Solvent and Nonaqueous Media", Journal of Pharmaceutical Sciences, vol. 66(8): 1076–1078, Aug. 1977.

Mark, H.F., et al.: "Kirk–Othmer Encyclopedia of Chemical Technology, Supplement Volume: Alcohol Fuels to Toxicology, Edition 3, " 1989, Wiley & Sons, US, New York, pp. 145–158.

PCT International Search Report:PCT/US98/00034.

*Primary Examiner*—Howard C. Lee
*Attorney, Agent, or Firm*—Thompson Hine & Flory LLP

[57] ABSTRACT

A method for removing a high boiling solvent from a pharmaceutical composition dissolved in the high boiling solvent comprising adding a low boiling co-solvent to the solution to form a mixture of the high boiling solvent and the low boiling co-solvent, and removing the solvent/co-solvent mixture under vacuum.

10 Claims, No Drawings

6,045,808

METHOD FOR REMOVING HIGH BOILING SOLVENTS FROM DRUG FORMULATIONS BY VACUUM DRYING

BACKGROUND OF THE INVENTION

The present invention relates to a method for the removal of high boiling solvents from drug formulations by vacuum drying the formulation in the presence of a low boiling co-solvent.

New pharmaceutical compounds such as anti-neoplastic drugs for treating cancer patients have been synthesized in increasing numbers in recent years. While most of these new drugs exhibit excellent pharmaceutical activity, they are often very difficult to recover from the reaction medium during their synthesis. In many cases the manufacture of such drugs require the use of a high boiling solvent (HBS). This solvent may be used in the reaction medium in which the drug is synthesized. High boiling solvents may also be employed in manufacturing the drug in a crystallization or an extraction process. Because of the extreme difficulty in removing the high boiling solvent from the solution containing the drug, the availability of the drugs whose manufacture or recovery involves high boiling solvents has been severely limited.

Accordingly, there is a need for a method whereby these high boiling solvents can be effectively removed from the drug-containing solution so that the drug can be reconstituted in a readily injectable form.

SUMMARY

It is a particular object of the present invention to provide a method for removing a high boiling, solvent from a solution of a pharmaceutical compound.

It is another object of the present invention to provide a method for preparing a pharmaceutical composition which is suitable, upon reconstitution, for treating a person suffering from cancer of other diseases.

In accordance with the present invention a high boiling solvent is effectively removed from a solution of a pharmaceutical compound dissolved in the high boiling solvent by adding a low boiling co-solvent to the solution of the pharmaceutical compound to form a mixture of the low boiling co-solvent and the high boiling solvent. The solution is placed under vacuum at a temperature which is greater than the freezing point of the solvent mixture and lower than the boiling point of the solvent mixture. Both the high boiling solvent and the low boiling co-solvent, can be effectively removed from the pharmaceutical compound to levels below detection.

DETAILED DESCRIPTION OF THE INVENTION

In the present invention the term "vacuum drying" refers to a drying technique in which a solution of a pharmaceutical compound in a solvent medium containing a mixture of a high boiling solvent and a low boiling co-solvent is subjected to vacuum at a temperature greater than the freezing point of the solvent mixture and less that the boiling point of the solvent mixture.

In the present invention, the term "mixture" when referring to the combination of the high boiling solvent and low boiling co-solvent means that the low boiling co-solvent is added to the high boiling solvent in an amount within the solubility limits of the low boiling co-solvent in the high boiling solvent and vice versa.

In accordance with the invention, pharmaceutical compounds which are ordinarily synthesized in the presence of high boiling solvents such as dimethyl sulfoxide (DMSO), dimethyl acetamide (DMA), dimethyl formamide (DMF), and the like can now be recovered by vacuum drying as described herein to provide a drug suitable, upon reconstitution, for treating a person suffering from cancer or other disease.

A technique has now been devised wherein a high boiling solvent can be removed from a drug compound dissolved in the high boiling solvent by vacuum drying in the presence of a low boiling co-solvent to levels below the detection limits of the high boiling solvent and low boiling co-solvent. While the method of removal of the high boiling solvent is not entirely understood, it is believed that the low boiling co-solvent augments the mass transfer rate of the high boiling solvent. It is also likely that there is some hydrogen bonding between the high boiling solvent and the low boiling co-solvent, which in turn leads to a volatilizing effect. The method does not depend on the formation of an azeotrope.

In accordance with the invention, a low boiling co-solvent is added to a solution of a pharmaceutical compound dissolved in a high boiling solvent and the formulation is vacuum dried to remove the high boiling solvent and the low boiling co-solvent. After vacuum drying, the drug compound can be reconstituted in a suitable solvent in an otherwise conventional manner to provide a drug formulation suitable for administration to a patient.

The present invention is particularly useful in preparing or formulating drugs which exhibit excellent pharmaceutical activity but are extremely difficult to recover from the high boiling solvent medium in which they are synthesized or manufactured. The drugs dissolved in the high boiling solvents generally are not acceptable as injectable formulations because of the toxicity or other objectional characteristics of the high boiling solvent medium.

The present technique can also be used to make finished dosage forms when the active drug substance is soluble in a high boiling solvent only and aqueous solutions render the moiety unstable.

The high boiling solvents used as a solvent medium in the synthesis of the pharmaceutical compounds according to the present invention are those organic compounds which exhibit a boiling point of about 100° C. or greater. Typical examples of such high boiling solvents include dimethyl sulfoxide (DMSO), dimethylacetamide (DMAC), dimethyl formamide (DMF), ortho, meta or para-toluidine, p-toluene sulfonic acid, toluene, pyridine, ortani, chlorobenzene, ethylbenzene, ortho, meta or para xylene, tetrachloroethane, cumene, propionic acid, 1-hexanol, m-butanol, and acetic acid.

The co-solvents found to be useful in the invention to remove the high boiling solvents are generally soluble in the high boiling solvent and vice versa, and they typically exhibit a boiling point of about 80° C. or less. Typical examples of such co-solvents are methanol, ethanol, isopropanol, methylene chloride, chloroform, carbon tetrachloride, ethyl acetate, acrylonitrile, butyraldehyde, m-hexane, methyl acetate, carbon disulfide, diethylamine, 1,1,1,-trichloroethane and the like. Ethanol is the preferred co-solvent because of its availability, efficiency and safety considerations.

The volume ratio of high boiling solvent to low boiling co-solvent is determined by the difference in vapor pressure of the two components and their mutual solubility with respect to each other. Typically, the ratio of solvent to co-solvent is about 10:1 to 1:10. The low boiling co-solvent is added to the solution of the pharmaceutical compound in the high boiling solvent in an amount and under conditions which prevent precipitation of the drug from the solution within the solubility limits of the high boiling solvent and low boiling co-solvent. While the manner in which the addition of the low boiling co-solvent enables removal of the high boiling solvent is not entirely clear, it is clear that the solvent and co-solvent do not necessarily form an azeotrope. Rather, the evaporation of the co-solvent appears to transport the high boiling solvent out of the solution.

Because of its effectiveness as a high boiling solvent/low boiling co-solvent mixture towards a large number of pharmaceutical compounds, the combined use of dimethyl sulfoxide/ethanol is preferred.

The process of this invention is particularly useful in the preparation of injectable pharmaceutical formulations, e.g., anti-neoplastic agents which were previously impossible to formulate because of their extreme instability in common injectable vehicles. Examples of such drugs include carmustine (BCNU) (a nitrosourea anti-tumor alkylatinf agent), PCNU, lomustine, Taxol, camptothecins, anthracyclines, etoposide, bizelesins and carzelesin to name a few.

In carrying out the method of the invention, a solution of the pharmaceutical compound in a high boiling solvent is vacuum dried in the presence of a co-solvent under conditions of temperature and pressure which would not be capable of removing the high boiling solvent alone, e.g., conditions at which the vapor pressure of the high boiling solvent would still be below the vacuum pressure. The vacuum level used can easily be determined by a person skilled in the art and is dependent upon the vapor pressures of the high boiling solvent and the low boiling co-solvent, the ratio of high boiling solvent to low boiling co-solvent, temperature, etc. Typically vacuum levels found to be effective are in the range of about 500 to 15,000 microns.

The temperature range is chosen such that the mixture of high boiling solvent and low boiling co-solvent neither freezes nor boils. Typically, the temperature will be in the range of about −50° C. to +25° C.

Upon removal of the solvent/co-solvent mixture, the pharmaceutical compound is reconstituted in a suitable solvent such as water, ethanol, polyethylene glycol-200 (PEG-200), polyethylene glycol 300 (PEG-300), PET (a mixture of polyethylene glycol, ethanol and Tween 80). Tween 80 is a polyoxyethylene (20) sorbitan monooleate available from Aldrich.

Vacuum drying of twelve formulations consisting of various mixtures containing dimethyl sulfoxide (DMSO) as the high boiling solvent and ethanol as the low boiling co-solvent was carried out to determine the effectiveness of such technique to remove the high boiling solvent/low boiling co-solvent mixture under vacuum. The results are shown in Table 1 below.

TABLE 1

Vacuum Drying DMSO/Ethanol Solutions
HPLC Assay Data

| | |
|---|---|
| Wavelength | 214 nm |
| Column | Zorbax C8 4.6 × 250 mm |
| Flowrate | 1.50 mL/min |
| Mobile Phase | 5% Methanol/95% Purified Water USP |

| Formulation | Vial Size (cc) | Neck Diameter (mm) | Fill Volume (mL) | DMSO Initial % | DMSO Final % |
|---|---|---|---|---|---|
| 1. DMSO/Ethanol | 2 | 13 | 1 | 50% | ND |
| 2. DMSO/Ethanol | 10 | 20 | 2 | 90% | ND |
| 3. DMSO/Ethanol | 10 | 20 | 2 | 10% | ND |
| 4. DMSO/Ethanol | 10 | 20 | 2 | 50% | ND |
| 5. DMSO/Ethanol | 10 | 20 | 5 | 90% | ND |
| 6. DMSO/Ethanol | 20 | 20 | 5 | 10% | ND |
| 7. DMSO/Ethanol | 20 | 20 | 5 | 50% | ND |
| 8. DMSO/Ethanol | 20 | 20 | 10 | 90% | ND |
| 9. DMSO/Ethanol/ Citrate | 10 | 20 | 2 | 10% | UD |
| 10. DMSO/Ethanol/ Citrate | 20 | 20 | 5 | 10% | UD |
| 11. DMSO/Ethanol/ PVP | 5 | 20 | 2 | 10% | UD |
| 12. DMSO/Ethanol/ PVP | 10 | 20 | 5 | 10% | UD |

UD—UnDetermined due to Peak Interference
ND—Not Detected
PVP—Polyvinylpyrrolidone In some cases it is desirable to add a pharmaceutically acceptable cake-forming agent or excipient to the pharmaceutical composition to enhance the characteristics of the composition such as color, texture, strength, and volume of the product. Examples of cake-forming agents or excipients useful in the invention are those materials which do not interact with the pharmaceutical compound and typically include polyvinyl pyrrolidone (PVP), citric acid, tartaric acid, sodium or potassium phosphate, gelatin, and carbohydrates such as mannitol, lactose, dextrose, dextran hetastarch, etc.

Other additives may be added to the formulation if desired. Such additives are those customarily added to pharmaceutical formulations.

While the invention is particularly useful in removing high boiling solvents from pharmaceutical compounds, the method described herein can also be used to remove other high boiling solvents used as a reaction medium or crystallizing and/or extracting medium in the manufacture of various other organic compounds.

Having described the invention in detail by reference to preferred embodiments thereof, it will be apparent that modifications and variations are possible without departing from the scope of the invention defined in the appended claims.

What is claimed is:

1. A method for removing dimethyl sulfoxide from a solution of an anti-neoplastic pharmaceutical compound in said dimethyl sulfoxide consisting essentially of adding ethanol to said solution in a weight ratio of dimethyl sulfoxide: ethanol of about 10:1 to 1:10, and removing said dimethyl sulfoxide and said ethanol by evaporation of said dimethyl sulfoxide and said ethanol under a vacuum of about 500 to 1500 microns and at a temperature of about −50° to +25° C.

2. The method of claim 1 wherein said anti-neoplastic pharmaceutical compound is a drug selected from the group consisting of carmustine, lomustine, taxol, camptothecins, anthrocyclines, PCNU, etopside, bizelesin and carzelesin.

3. The method of claim 1 wherein said pharmaceutical compound is vacuum dried and reconstituted in a suitable solvent to provide a formulation suitable for administration to a patient.

4. The method of claim 1 wherein said pharmaceutical compound is vacuum dried and reconstituted in a suitable solvent to provide a formulation suitable for administration to a patient.

5. The method of claim 1 wherein said method is conducted in the absence of water.

6. The method of claim 1 wherein said method is conducted in the absence of water.

7. A method for removing a high boiling solvent selected from the group consisting of dimethyl sulfoxide, dimethyl acetamide, dimethyl formamide, ortho-toluidine, meta-toluidine, para-toluidine, p-toluene sulfonic acid, toluene, pyridine, chlorobenzene, ethylbenzene, ortho-xylene, meta-xylene, para-xylene, tetrachloroethane, cumene, propionic acid, 1-hexanol, n-butanol, and acetic acid from a solution of a pharmaceutical compound in said high boiling solvent, said method consisting essentially of adding a low boiling solvent selected from the group consisting of ethanol, methanol, isopropanol, methylene chloride, chloroform, carbon tetrachloride, ethyl acetate, acrylonitrile, butyraldehyde, n-hexane, methyl acetate, carbon disulfide, diethylamine, and 1,1,1-trichloroethane to the solution in a weight ratio of high boiling solvent:low boiling solvent of about 10:1 to 1:10 and removing said high boiling solvent along with said low boiling solvent by evaporation of said high boiling solvent and said low boiling solvent under a vacuum of about 500 to 1500 microns and at a temperature of about −50° C. to +25° C.

8. The method of claim 7 wherein said method is conducted in the absence of water.

9. The method of claim 7 wherein said pharmaceutical compound is vacuum dried and reconstituted in a suitable solvent to provide a formulation suitable for administration to a patient.

10. The method of claim 7 wherein the pharmaceutical compound is selected from the group consisting of carmustine, lomustine, taxol, camptothecins, anthracyclines, PCNU, etoposide, bizelesin, and carzelesin.

* * * * *

UNITED STATES PATENT AND TRADEMARK OFFICE
CERTIFICATE OF CORRECTION

PATENT NO.    : 6,045,808
DATED         : April 4, 2000
INVENTOR(S)   : Mathew Cherian It is certified that error appears in the above-identified patent and that said Letters Patent is hereby corrected as shown below:

Cancel claims 3 and 5.

Signed and Sealed this

Third Day of April, 2001

*Attest:*

NICHOLAS P. GODICI

*Attesting Officer*     *Acting Director of the United States Patent and Trademark Office*